US012324750B2

(12) United States Patent
Paterson et al.

(10) Patent No.: US 12,324,750 B2
(45) Date of Patent: Jun. 10, 2025

(54) SHIELD GUIDE ASSEMBLY

(71) Applicant: Arthrex, Inc., Naples, FL (US)

(72) Inventors: John David Paterson, Naples, FL (US); Kevin John Gallen, Naples, FL (US); James Tyler Clevett, Bonita Springs, FL (US); Steven P. Schewe, Bradenton, FL (US); Frank Uhing, Munich (DE); Michael Stephan van der Merwe, Munich (DE); Bernd Felkel, Landsberg am Lech (DE); Matthew John Ravenscroft, Congleton (GB); Justin William Griffin, Virginia Beach, VA (US)

(73) Assignee: ARTHREX, INC., Naples, FL (US)

( * ) Notice: Subject to any disclaimer, the term of this patent is extended or adjusted under 35 U.S.C. 154(b) by 1048 days.

(21) Appl. No.: 17/214,067

(22) Filed: Mar. 26, 2021

(65) Prior Publication Data
US 2022/0304828 A1 Sep. 29, 2022

(51) Int. Cl.
*A61F 2/46* (2006.01)
*A61B 17/17* (2006.01)
*A61F 2/40* (2006.01)
*A61B 90/00* (2016.01)

(52) U.S. Cl.
CPC ........ *A61F 2/4612* (2013.01); *A61B 17/1778* (2016.11); *A61F 2/4014* (2013.01); *A61B 2090/0801* (2016.02)

(58) Field of Classification Search
CPC ................. A61F 2/4612; A61B 2090/0801
See application file for complete search history.

(56) References Cited

U.S. PATENT DOCUMENTS

| | | | |
|---|---|---|---|
| 9,005,184 B2 | 4/2015 | Mayer et al. | |
| 9,370,428 B2 | 6/2016 | Winslow et al. | |
| 9,974,658 B2 | 5/2018 | Chudik | |
| 2010/0145345 A1 | 6/2010 | Ammann et al. | |
| 2013/0096564 A1* | 4/2013 | Winslow | A61B 17/15 606/96 |
| 2016/0374698 A1 | 12/2016 | Kurtz | |

(Continued)

FOREIGN PATENT DOCUMENTS

| | | |
|---|---|---|
| AU | 2018232817 | 9/2019 |
| EP | 0637434 | 2/1995 |
| EP | 2116199 | 11/2009 |

(Continued)

OTHER PUBLICATIONS

International Search Report and Written Opinion for International Application No. PCT/US2022/020488 mailed Jun. 28, 2022.

(Continued)

*Primary Examiner* — Ariana Zimbouski
*Assistant Examiner* — Christine L Nelson
(74) *Attorney, Agent, or Firm* — Carlson, Gaskey & Olds, P.C.

(57) ABSTRACT

This disclosure relates to shield guide assembly and methods for restoring functionality to a joint. The shield guide assembly disclosed herein include a shield dimensioned to block access through the shield onto an adjacent bone surface region during formation of one or more features along the surgical site.

30 Claims, 14 Drawing Sheets

(56) References Cited

U.S. PATENT DOCUMENTS

2017/0095339 A1  4/2017  Frankle

FOREIGN PATENT DOCUMENTS

| WO | 2007092841 | 8/2007 |
| WO | 2014035991 | 3/2014 |
| WO | 2019060780 | 3/2019 |

OTHER PUBLICATIONS

International Preliminary Report on Patentability for International Application No. PCT/US2022/020488 mailed Oct. 5, 2023.

\* cited by examiner

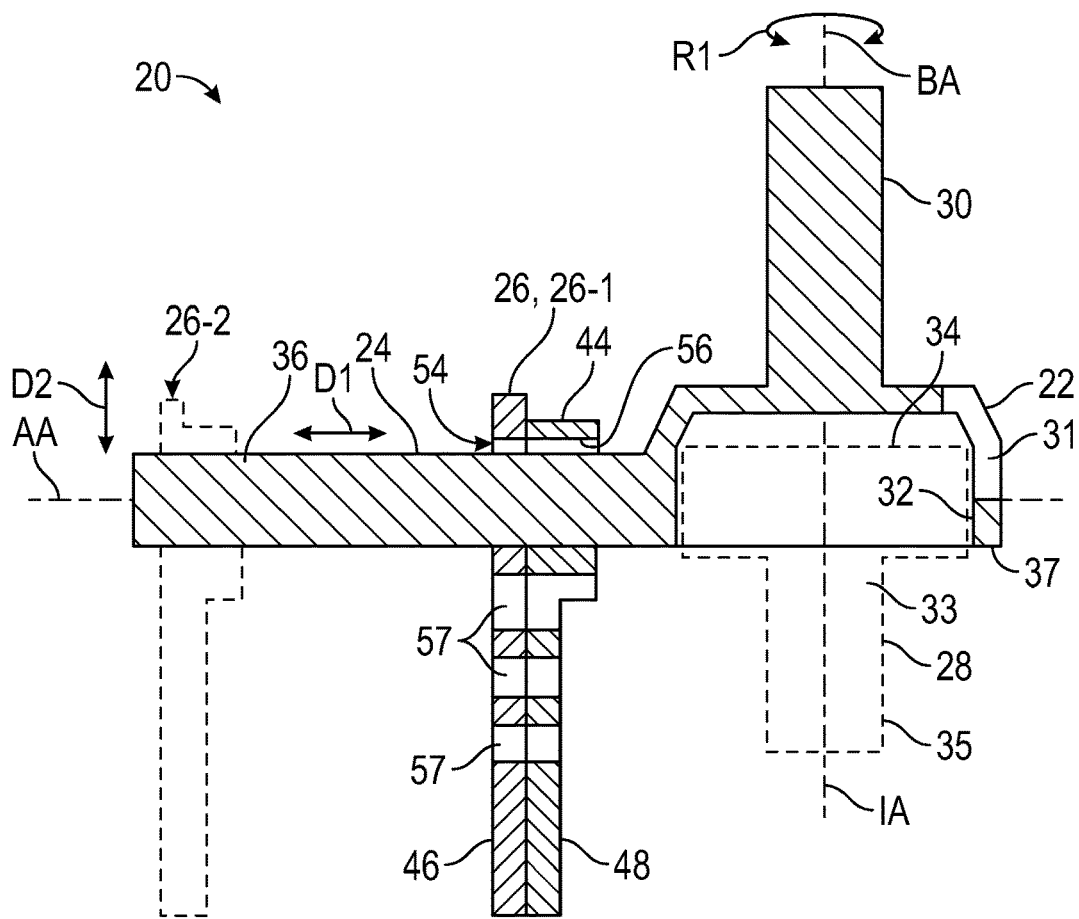
FIG. 3
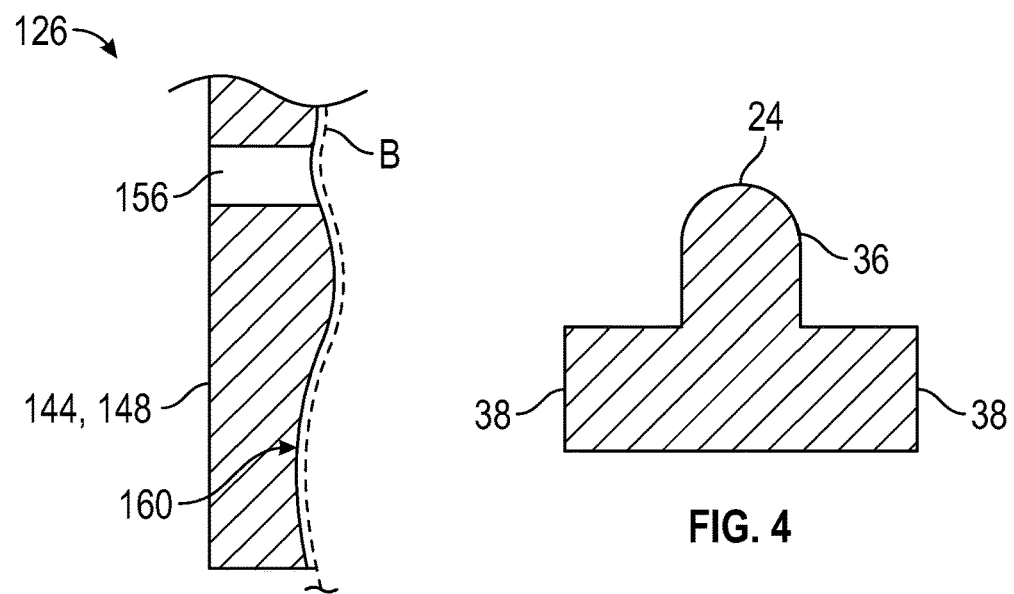
FIG. 3A
FIG. 4

SHIELD GUIDE ASSEMBLY

BACKGROUND

This disclosure relates to orthopaedic procedures and, more particularly, to a shield guide assembly for repairing a joint.

Many bones of the human musculoskeletal system include articular surfaces. The articular surfaces cooperate to facilitate different types and degrees of joint movement. The articular surfaces may erode or experience bone loss over time due to repeated use or wear or may fracture as a result of a traumatic impact. These types of bone defects may cause joint instability and pain. Some techniques may utilize a prosthesis to repair the articular surfaces. Tissue may be detached from the bone prior to placement of the prosthesis. The tissue may be reattached to the bone utilizing one or more fasteners situated adjacent to the prosthesis.

SUMMARY

This disclosure relates to shield guide assembly for an orthopaedic procedure. The shield guide assembly may be used to at least partially block access to a localized surface region of a bone during preparation of the surgical site.

A shield guide assembly for an orthopaedic procedure according to an exemplary aspect of this disclosure may include, inter alia, a base configured to be releasably secured to an implant, an elongated guide arm extending along an arm axis from the base, and a shield translatable along the arm axis to set a position of the shield relative to the base. The shield may include a shield body establishing a shield perimeter. The shield body may be dimensioned to block access through the shield body onto an adjacent bone surface region associated with a projection of the shield perimeter.

A shield guide assembly for an orthopaedic procedure according to an exemplary aspect of this disclosure may include, inter alia, a base configured to be releasably secured to an implant, a guide arm extending from the base, and a shield moveable relative to the guide arm. The shield includes a shield body that may be dimensioned to block access through the shield such that a projection of a perimeter of the shield body may silhouette a perimeter of the implant.

A kit for an orthopaedic procedure according to an exemplary aspect of this disclosure may include, inter alia, an implant including an implant body configured to be at least partially received in bone and a shield guide assembly. The shield guide assembly may include a base configured to be releasably secured to the implant, a guide arm extending from the base, and a shield translatable along a length of the guide arm to set a position of the shield relative to the implant. The shield may include a shield body establishing a shield perimeter. The shield body may be dimensioned to block access through the shield body onto an adjacent bone surface region of the bone associated with a projection of the shield perimeter.

A method of installing an orthopaedic implant according to an exemplary aspect of this disclosure may include, inter alia, positioning an implant in bone and securing a shield guide assembly to the implant. The shield guide assembly may include a base, a guide arm extending from the base, and a shield secured to the guide arm. The securing step may include mounting the base to the implant. The method may include moving the shield along the guide arm to set a position of the shield relative to the implant. The shield body may be dimensioned to block access through the shield body onto a bone surface region of the bone associated with a projection of the shield perimeter from the set position. The method may include forming at least one aperture in the bone adjacent to the bone surface region and the shield.

BRIEF DESCRIPTION OF THE DRAWINGS

FIG. 3 illustrates a sectional view of the shield guide assembly taken along line 3-3 of FIG. 2.

FIG. 3A illustrates a profile of an example shield.

FIG. 4 illustrates a sectional view of the shield guide assembly taken along line 4-4 of FIG. 2.

DETAILED DESCRIPTION

Figure 1:
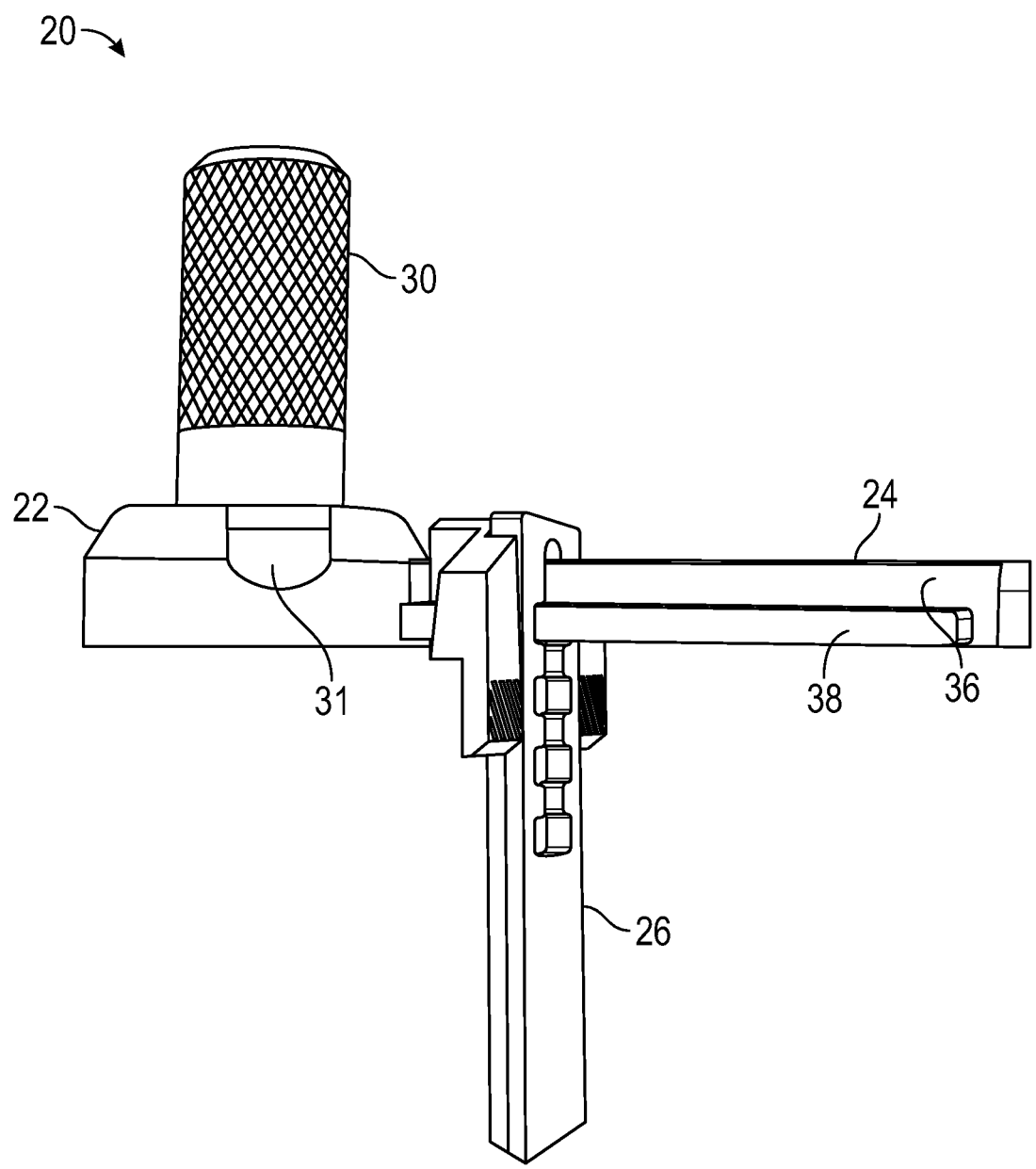
FIG. 1 illustrates a perspective view of an exemplary shield guide assembly including a base, guide arm and shield.

This disclosure relates to a shield guide assembly that may be utilized in an orthopaedic procedure for restoring functionality to a joint. The shield guide assembly described herein may be utilized during placement of a shoulder prosthesis in anatomical and reverse procedures for restoring functionality to shoulders having advanced cartilage disease. Visibility of portions of the prosthesis may be obscured due to placement in bone. The shield guide assembly and techniques disclosed herein may be utilized to block access to portions of the bone surrounding the prosthesis, thereby reducing a likelihood of contact from instrumentation and other devices that may be utilized for reattachment of any tissue that stabilizes a joint, such as soft tissue including tendons, ligaments and joint capsules, and other tissue, which may lead to improved healing. The tissue may include one or more rotor cuff tendons including a supraspinatus tendon, infraspinatus tendon, teres minor tendon and/or subscapularis tendon. For example, the surgeon may position the shield guide assembly relative to the prosthesis to reduce a likelihood of inadvertently contacting and forming holes into the prosthesis when preparing to reattach a subscapularis or other rotor cuff tendon to the bone.

A shield guide assembly for an orthopaedic procedure according to an exemplary aspect of this disclosure may include, inter alia, a base configured to be releasably secured to an implant, an elongated guide arm extending along an arm axis from the base, and a shield translatable along the arm axis to set a position of the shield relative to the base. The shield may include a shield body establishing a shield perimeter. The shield body may be dimensioned to block access through the shield body onto an adjacent bone surface region associated with a projection of the shield perimeter.

In a further embodiment, the shield body may include at least one slot configured to slidably receive a portion of the guide arm along the arm axis.

In a further embodiment, a length of the guide arm may have a T-shaped cross section.

In a further embodiment, the at least one slot may be a row of interconnected T-shaped slots corresponding to respective radial positions of the shield relative to the arm axis, and the length of the guide arm may be insertable into each one of the T-shaped slots to set the respective radial position of the shield.

In a further embodiment, the shield body excludes any apertures between the row of slots and the shield perimeter.

In a further embodiment, the base may include a recess configured to at least partially receive an end portion of the implant.

In a further embodiment, the base may be rotatable about an implant axis of the implant to vary a circumferential position of the shield relative to the implant axis.

In a further embodiment, the shield may be dimensioned to abut the adjacent bone surface region in an installed position.

In a further embodiment, the adjacent bone surface region may be associated with a humerus.

A shield guide assembly for an orthopaedic procedure according to an exemplary aspect of this disclosure may include, inter alia, a base configured to be releasably secured to an implant, a guide arm extending from the base, and a shield moveable relative to the guide arm. The shield includes a shield body that may be dimensioned to block access through the shield such that a projection of a perimeter of the shield body may silhouette a perimeter of the implant.

In a further embodiment, the base may be rotatable about an implant axis of the implant to vary a circumferential position of the shield relative to an implant axis of the implant.

In a further embodiment, the perimeter of the shield may be offset outwardly by a maximum distance of no more than 1 millimeter from the perimeter of the implant for substantially all positions along the perimeter of the implant below a bottom of the base relative to the implant axis.

In a further embodiment, the shield may be moveable relative to the guide arm to vary a radial position of the shield relative to the implant axis.

In a further embodiment, the shield body may be dimensioned to block access through the shield onto an adjacent bone surface region associated with a humerus.

A kit for an orthopaedic procedure according to an exemplary aspect of this disclosure may include, inter alia, an implant including an implant body configured to be at least partially received in bone and a shield guide assembly. The shield guide assembly may include a base configured to be releasably secured to the implant, a guide arm extending from the base, and a shield translatable along a length of the guide arm to set a position of the shield relative to the implant. The shield may include a shield body establishing a shield perimeter. The shield body may be dimensioned to block access through the shield body onto an adjacent bone surface region of the bone associated with a projection of the shield perimeter.

In a further embodiment, the shield perimeter may define a shield width that is greater than an implant width of the portions of the implant configured to be received in bone.

In a further embodiment, the implant body may extend along an implant axis between first and second end portions. The base may be configured to be secured to the first end portion. The shield may be rotatable about the implant axis to vary a circumferential position of the shield relative to the implant body in an installed position.

In a further embodiment, the implant may include a trunnion configured to be secured to the implant body and an articulation head configured to be secured to the implant body. The trunnion may be configured to engage a resected surface along a humerus. The articulation head may include an articulating face dimensioned to interface with an opposed articular surface associated with a glenoid or a glenoid implant.

In a further embodiment, a plurality of threads may extend about a circumference of the implant body, and the plurality of threads may be dimensioned to secure the implant body in bone.

A method of installing an orthopaedic implant according to an exemplary aspect of this disclosure may include, inter alia, positioning an implant in bone and securing a shield guide assembly to the implant. The shield guide assembly may include a base, a guide arm extending from the base, and a shield secured to the guide arm. The securing step may include mounting the base to the implant. The method may include moving the shield along the guide arm to set a position of the shield relative to the implant. The shield body may be dimensioned to block access through the shield body onto a bone surface region of the bone associated with a projection of the shield perimeter from the set position. The method may include forming at least one aperture in the bone adjacent to the bone surface region and the shield.

In a further embodiment, the tissue may be soft tissue, and the method may include positioning a fastener in the at least one aperture to secure the soft tissue to the bone.

In a further embodiment, the bone may be a humerus, the fastener may be a suture anchor, and the soft tissue may include a subscapularis tendon.

In a further embodiment, the bone may be a humerus. The method may include resecting the humerus along a humeral head to establish a resected surface, and then embedding at least a portion of the implant in the resected surface.

In a further embodiment, the method may include rotating the shield about an implant axis of the implant to set a circumferential position of the shield relative to the implant. The moving step may occur such that the shield abuts the bone along the bone surface region in the set position. The forming step may occur subsequent to the rotating step and the moving step.

In a further embodiment, the bone may be a humerus. The method may include resecting the humerus along a humeral head to establish a resected surface, and then embedding at least a portion of the implant in the resected surface.

In a further embodiment, the implant may include an implant body, a trunnion configured to be secured to the implant body, and an articulation head. The articulation head may include an articulating face dimensioned to interface with an opposed articular surface associated with a glenoid or a glenoid implant. The step of positioning the implant may include moving the trunnion into engagement along the resected surface.

In a further embodiment, a plurality of threads may extend about a circumference of the implant body. The step of positioning the implant may include rotating the implant body about an implant axis to fixedly attach the implant body in the bone. The method may include securing the articulation head to the trunnion to trap an end portion of the implant body between the trunnion and the articulation head.

FIGS. 1-6 illustrate an exemplary shield guide assembly 20. The assembly 20 may be utilized for various surgical procedures, such as orthopaedic procedures for restoring functionality of a joint. The assembly 20 may be utilized in the repair of articular surfaces along a humerus in anatomical and reverse shoulder replacement procedures. The assembly 20 may be utilized during attachment of soft tissue including tendons, ligaments and joint capsules, and other tissue at a surgical site, such as reattachment of a subscapularis or other rotator cuff tendon to bone subsequent to implantation of a prosthesis in the humerus. The surgeon may situate the assembly 20 to block a pathway to portions of the bone surrounding the implant during preparation of the surgical site, thereby reducing a likelihood of contact from instrumentation and other devices such as guide pins and fasteners that may be utilized for attachment of the tissue. Although the assembly disclosed herein primarily refer to shoulder reconstructions, the disclosed assembly may be utilized to restore functionality to other locations of the patient, such as knee and hip joints.

Referring to FIG. 1, the assembly 20 includes a base 22, an elongated guide arm 24 and a shield 26 carried by and secured to the guide arm 24. The base 22 is configured to be releasably secured to an implant 28 (shown in dashed lines in FIG. 3 for illustrative purposes). The assembly 20 may be utilized with implants of various shapes and sizes. A geometry of the implant 28 of FIG. 3 is exemplary and is not intended to be limiting. The shield 26 is translatable along a length of the guide arm 24 to set a position of the shield 26 relative to the base 22 and the implant 28.

Figure 2:
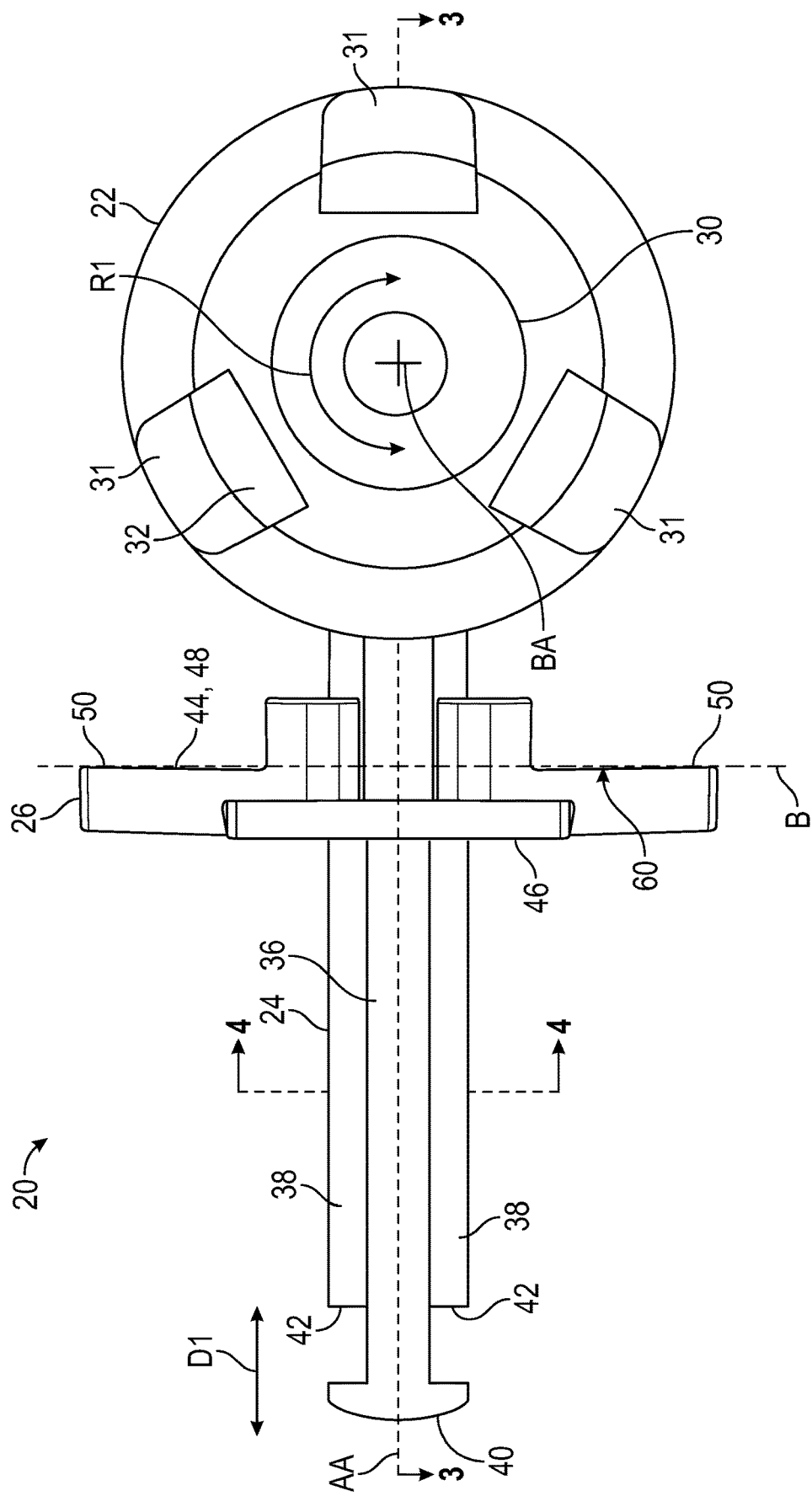
FIG. 2 illustrates a plan view of the shield guide assembly of FIG. 1.

Referring to FIGS. 2 and 3, with continuing reference to FIG. 1, the base 22 may have a generally dome shaped geometry for interfacing with the implant 28 (FIG. 3). The base 22 may extend along a base axis BA. The assembly 20 may include a handle 30 extending outwardly from the base 22, such as along the base axis BA as illustrated in FIG. 3. The handle 30 may be dimensioned for manipulation by the surgeon to place the assembly 20 at a desired position and/or orientation along a surgical site. The handle 30 may have a generally cylindrical-shaped geometry. The handle 30 may be integrally formed with the base 22 or may be a separate and distinct component mechanically attached to the base 22 with one or more fasteners.

The base 22 may include a recess 32 configured to at least partially receive a first end portion 34 of the implant 28 to secure the base 22 to the implant 28, as illustrated in FIG. 3. The base 22 may define one or more openings 31 (e.g., windows) for viewing the first end portion 34 of the implant 28, which may assist in positioning of the assembly 20. The implant 28 may include an implant body 33 extending along an implant axis IA between a first end portion 34 and a second end portion 35. The base axis BA may be collinear or otherwise substantially parallel to the implant axis IA of the implant 28 in an installed position, as illustrated in FIG. 3. In other implementations, the base 22 may be dimensioned such that the base axis BA is transverse to the implant axis IA. For the purposes of this disclosure, the terms "about," "approximately" and "substantially" mean within ±10% of the stated value or relationship unless otherwise indicated. The recess 32 may be dimensioned to have a geometry that complements a periphery of the first end portion 34 of the implant 28.

The base 22 may be rotatable in a direction R1 about the implant axis IA to vary a circumferential position of the shield 26 relative to the implant axis IA and implant body 33 of the implant 28 in an installed position. In other implementations, the recess 32 is dimensioned to establish an interference fit with the periphery of the implant body 33 to limit or otherwise oppose relative rotation.

The guide arm 24 may be cantilevered from a periphery of the base 22. The guide arm 24 may extend along an arm axis AA from the base 22. The guide arm 24 may be dimensioned such that the arm axis AA is substantially perpendicular to the base axis BA and such that the shield 26 is substantially parallel to the base axis BA, as illustrated in FIG. 3. In other implementations, the assembly 20 may be dimensioned such that the shield 26 is substantially non-parallel to the base axis BA and angled relative to the base 22. The shield 26 is translatable in a direction D1 along the arm axis AA to set a position of the shield 26 relative to the base 22. Exemplary positions of the shield 26 along the guide arm 24 are illustrated by shields 26-1, 26-2 in FIG. 3 (26-2 indicated in dashed lines for illustrative purposes). The periphery of the base 22 may define the axially innermost position of the shield 26 relative to the arm axis AA. Moving the shield 26 in the direction D1 along the guide arm 24 may occur such that the shield 26 abuts bone B in the set position (bone B shown in dashed lines in FIG. 2 for illustrative purposes).

The guide arm 24 may be dimensioned to limit rotation of the shield 26 about the arm axis AA. In other implementations, the shield 26 may be rotatable about the arm axis AA. The guide arm 24 may include a main body 36 extending along the arm axis AA and a pair of rails 38 (FIG. 2) on opposed sides of the main body 36. The rails 38 may be arranged along the main body 36 such that a length of the guide arm 24 has a substantially T-shaped cross-sectional geometry, as illustrated in FIG. 4. The rails 38 may be dimensioned to extend from the periphery of the base 22 and may be spaced apart from an abutment 40 at a free end of the guide arm 24 to establish a pair of opposed slots 42 (FIG. 3). The abutment 40 may define an axially outermost position of the shield 26 relative to the arm axis AA.

The shield 26 may include a shield body 44 dimensioned with respect to a predetermined implant geometry to block a pathway or access through the shield body 44 onto an adjacent localized bone surface region, such as during formation of one or more apertures utilized for reattachment of tissue, including any tissue disclosed herein, such as a subscapularis or other rotator cuff tendon subsequent to at least partially embedding the implant 28 in bone.

Figure 5:
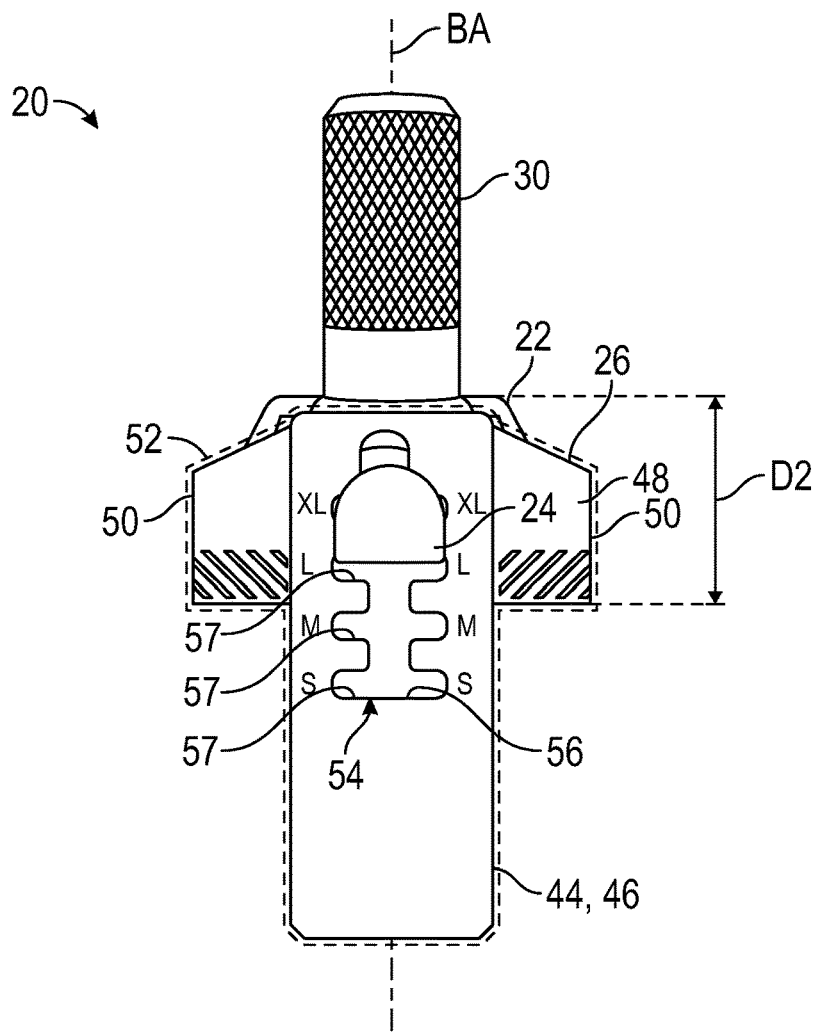
FIG. 5 illustrates an end view of the shield guide assembly of FIG. 1.

Referring to FIG. 5, with continuing reference to FIGS. 2-3, the shield body 44 may include a first portion 46 and a second portion 48. The first portion 46 may face towards the free end of the guide arm 24, and the second portion 48 may face towards the base 22. The first and second portions 46, 48 may be integrally formed or may be separate and distinct components mechanically attached or otherwise secured to each other. The first portion 46 may have a substantially rectangular geometry. The second portion 48 may include a pair of wings 50 dimensioned to extend outwardly of the first portion 46. The first and second portions 46, 48 of the shield body 44 cooperate to establish a shield perimeter 52 (shown in dashed lines for illustrative purposes).

The shield body 44 may be dimensioned with respect to a geometry of the surgical site. The shield body 44 may have a substantially planar geometry along the second portion 48, as illustrated in FIG. 3. In other implementations, the shield 26 may be dimensioned to substantially complement or approximate a contour of an adjacent surface of bone B, as illustrated by shield body 144 in FIG. 3A. Contouring the shield body 144 may reduce a likelihood of placing instrumentation and other devices between the shield body 144 and the bone B. In this disclosure, like reference numerals designate like elements where appropriate and reference numerals with the addition of one-hundred or multiples thereof designate modified elements that are understood to incorporate the same features and benefits of the corresponding original elements.

Figure 5A:
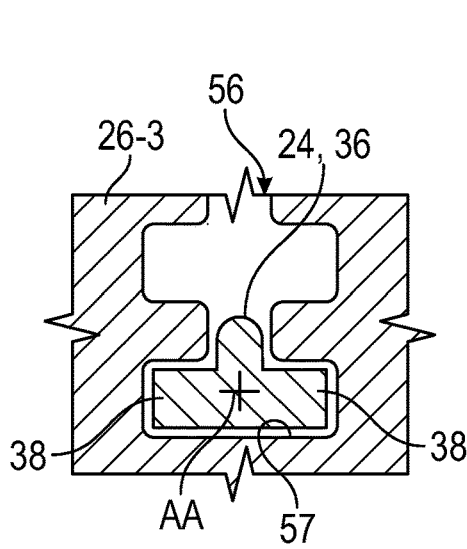
FIGS. 5A-5B illustrate the shield in first and second positions relative to the guide arm.
Figure 5B:
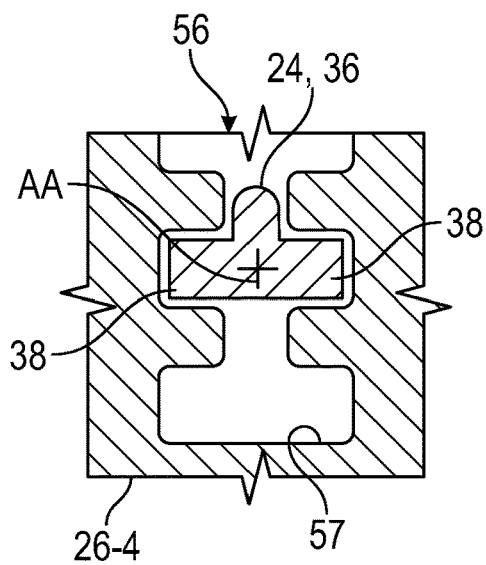

The shield 26 may be moveable relative to the guide arm 24 to vary a radial position of the shield 26 relative to the implant axis IA of the implant 28. The shield body 44 may include at least one slot 54 extending through the first and second portions 46, 48. The slot 54 is configured to slidably receive a portion of the guide arm 24 along the arm axis AA, as illustrated in FIG. 3. The slot 54 may have various geometries such as a row of interconnected T-shaped slots 57. The T-shaped slots 57 may correspond to respective radial positions of the shield 26 relative to the arm axis AA and/or a set of predetermined implant size(s). For example, the shield body 44 may define four slots 57 corresponding to a set of predetermined implant size(s) (e.g., small, medium, large, and extra-large). The shield body 44 may be aligned with one of the slots 57 in the guide arm 24, and then the shield 26 may be moved in a direction D2 to set the radial position of the shield 26 relative to the arm axis AA, as illustrated by shields 26-3, 26-4 in FIGS. 5A-5B. The rails 38 along the length of the guide arm 24 may be insertable into each one of the T-shaped slots 57 to set the radial position of the shield 26 relative to the arm axis AA. The shield 26 may be dimensioned such that the shield body 44 excludes any apertures between the row of slots 57 and the shield perimeter 52, as illustrated in FIG. 5.

Figure 6:
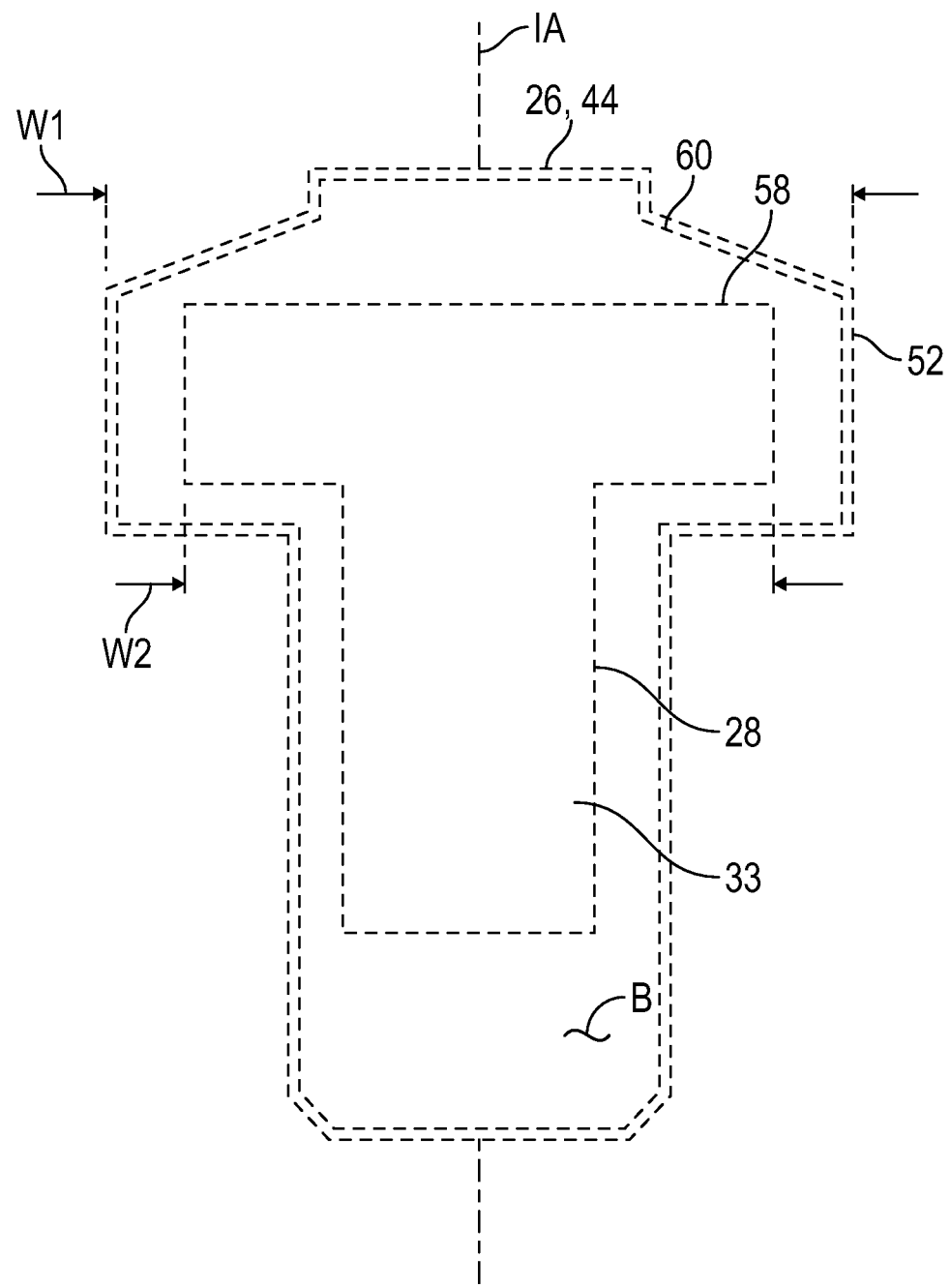
FIG. 6 illustrates a shield perimeter of the shield guide of FIG. 5 relative to a localized bone surface region and implant perimeter.

Referring to FIG. 6, with continuing reference to FIGS. 3 and 5, the shield perimeter 52 may be dimensioned with respect to a predetermined geometry of an implant or set of implants. For example, the implant 28 may establish an implant perimeter 58. The implant perimeter 58 may correspond to portions of the implant 28 configured to be received in bone, or may correspond to an entirety of the implant 28 including portions configured to extend outwardly from bone. The shield perimeter 52 may be dimensioned such that a projection of the shield perimeter 52 substantially or completely surrounds the implant perimeter 58. The shield 26 may be dimensioned to block access through the shield body 44 onto an adjacent localized bone surface region 60 associated with a projection of the shield perimeter 52. The bone surface region 60 may be established along an external surface contour of a bone B that at least partially receives the implant 28, such as a humeral head. The shield 26 may be dimensioned to abut the bone surface region 60 in an installed position, as illustrated in FIG. 2 (see also FIG. 3A). The shield perimeter 52, implant perimeter 58, bone surface region 60 and related features are shown in dashed lines in FIG. 6 for illustrative purposes.

Figure 7:
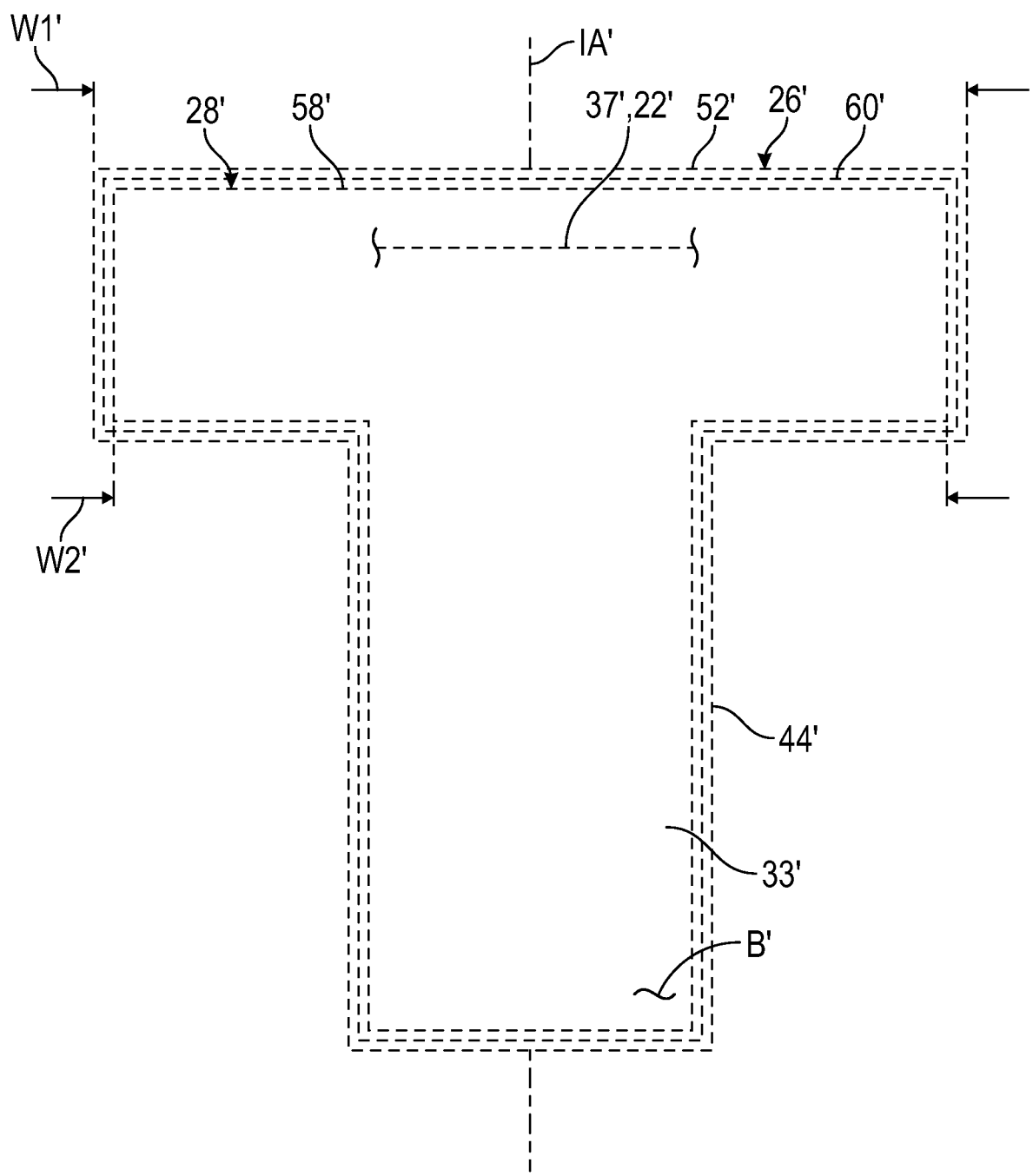
FIG. 7 illustrates a shield perimeter of another shield guide relative to an implant perimeter.

The perimeter 52 of the shield 26 may establish a first width W1. The first width W1 may extend between a pair of lateral walls of the shield body 44. The perimeter 58 of the implant 28 may establish a second width W2. The shield body 44 may be dimensioned such that the shield width W1 is greater than the implant width W2 for at least portions of the implant 28 configured to be received in bone, as illustrated by FIG. 6. The shield 26 may be dimensioned to have a height that is greater than or equal to a height of the implant body 33 such that the perimeter 52 of the shield 26 extends above and/or below the perimeter 58 of the implant 28 relative to the implant axis IA, as illustrated in FIG. 3. As illustrated in FIG. 7, shield 26' may be dimensioned to closely approximate a profile of implant 28'. A perimeter 52' of the shield 26' may be dimensioned to substantially follow a perimeter 58' of the implant 28' such that a projection of the perimeter 52' of the shield 26' silhouettes the perimeter 58' of the implant 28' to block access through the shield body 44' onto an adjacent localized bone surface region 60'. A first width W1' of the shield 26' may be substantially equal to a second width W2' of the implant 28'. The perimeter 52' of the shield 26' may be offset outwardly by a maximum distance of no more than 1 millimeter (mm) from the perimeter 58' of the implant 28' for at least a majority or substantially all positions along the perimeter 58', including at least positions of the perimeter 58' below a bottom 37' of base 22' relative to implant axis IA' (see also bottom 37 of base 22 in FIG. 3). The disclosed techniques may facilitate more closely positioning instrumentation relative to the implant 28' during formation of one or more features in bone B', which may improve fixation and healing of the patient.

Figure 8:
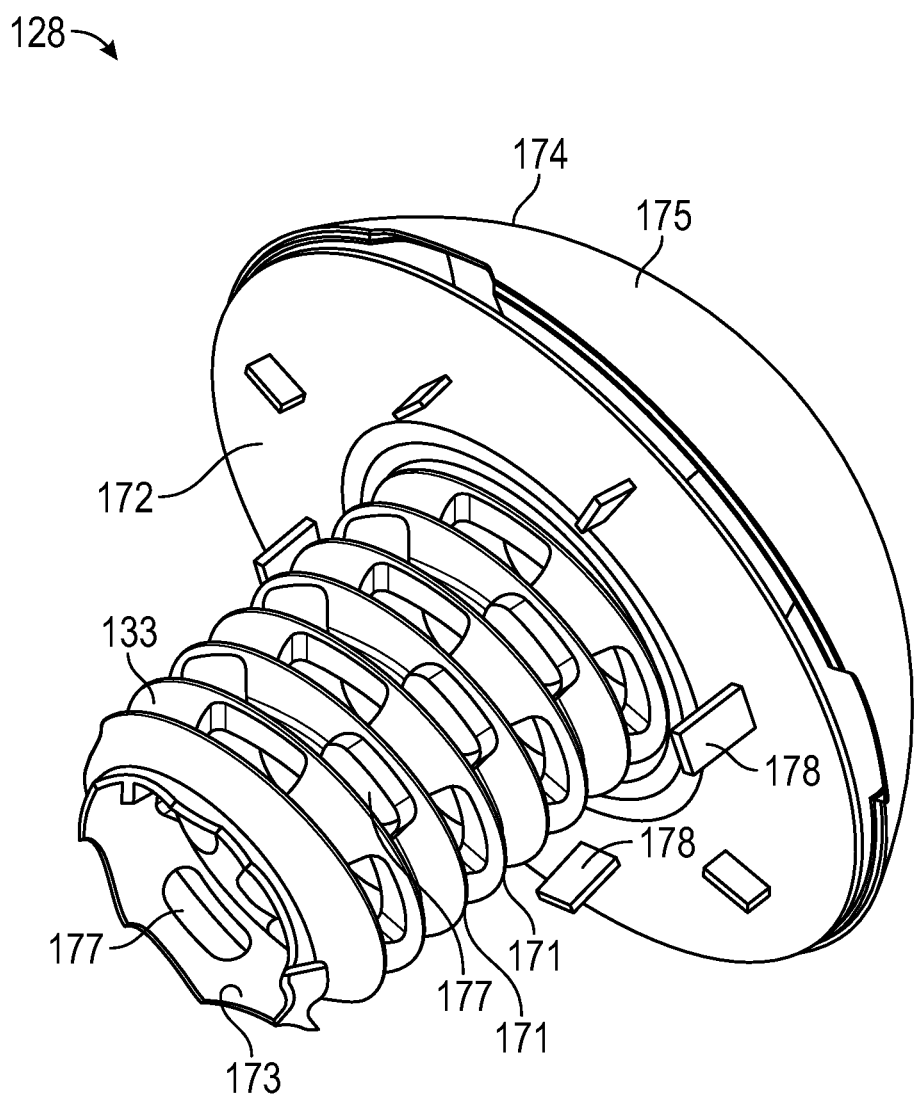
FIGS. 8-9 illustrate perspective and exploded views of an exemplary implant.
Figure 9:
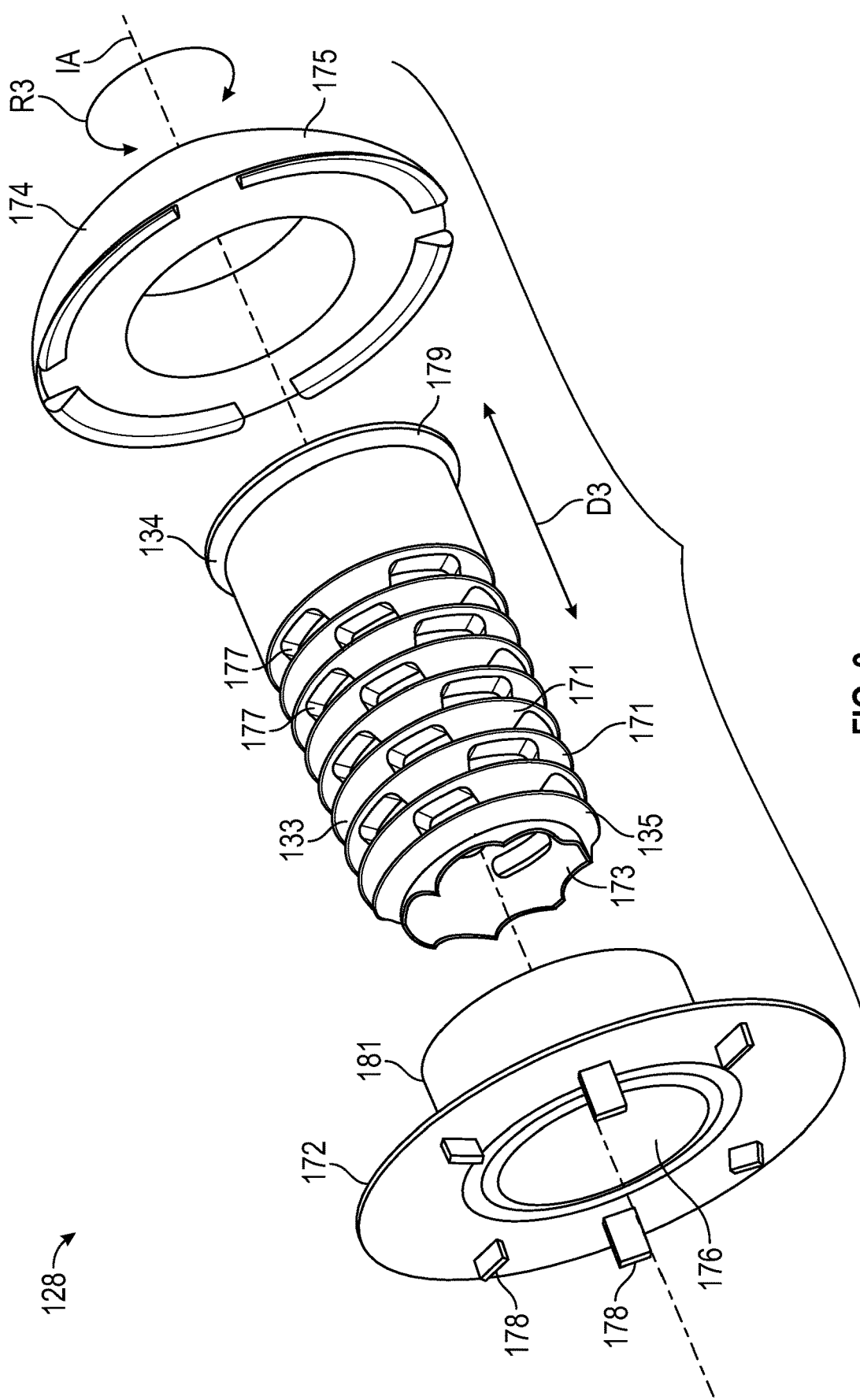

FIGS. 8-9 illustrate an exemplary orthopaedic implant 128 that may be utilized with the shield guide assembly 20. The implant 128 may be representative of a stemless implant sold under the tradename Eclipse System™ and manufactured by Arthrex®, Inc. The assembly 20 and disclosed implants may be provided to the surgeon as a kit for performing an orthopaedic procedure. The kit may include implants of various shapes and sizes. The particular implant may be selected from the kit according to an anatomy of the patient. Other implants may be utilized with the teachings disclosed herein, including implants having a stem portion received within an internal cavity of a bone, intramedullary nails, and bone plates.

The implant 128 may include an implant body 133, a trunnion 172 and an articulation head 174. The implant body 133 may be configured to be at least partially received in bone, such as along a resected surface of a humeral head. The implant body 133 may be a cage screw including one or more threads 171 extending about a circumference of the implant body 133. The threads 171 may be dimensioned to secure the implant body 133 in bone. The implant body 133 may be rotatable in a direction R3 (FIG. 9) about an implant axis IA to secure the implant body 133 in bone. The implant body 133 may define a hollow cavity 173 and one or more openings 177 in a wall of the implant body 133. The openings 177 may promote bone growth from surrounding bone into the cavity 173, which may improve healing of the patient.

The trunnion 172 may be configured to be secured to the implant body 133. The trunnion 172 may be configured to engage a resected surface of a bone, such as a resected surface along a humerus (see, e.g., FIG. 12). The trunnion 172 may include a passage 176 (FIG. 9) configured to at least partially receive the implant body 133 along the implant axis IA. During assembly, the implant body 133 may be moved in a direction D3 along the implant axis IA and into the passage 176 until a collar 179 of the implant body 133 abuts a main body 181 of the trunnion 172. The trunnion 172 may include one or more protrusions 178 configured to engage a bone surface for securing the implant 128.

The articulation head 174 may be configured to be secured to the implant body 133. The articulation head 174 may include an articulating face 175 dimensioned to interface with an opposed articulated surface. The opposed articulated surface may be associated with a glenoid or a glenoid implant utilized in an anatomic or reverse shoulder repair procedure. The articulating face 175 may have a convex geometry for an anatomical shoulder procedure, as illustrated in FIGS. 8-9, or may have a concave face for a reverse shoulder procedure. The articulation head 174 may be moved in the direction D3 along the implant axis IA and impacted on, or otherwise secured to, the implant body 133 and/or main body 181 of the trunnion 172.

Figure 10:
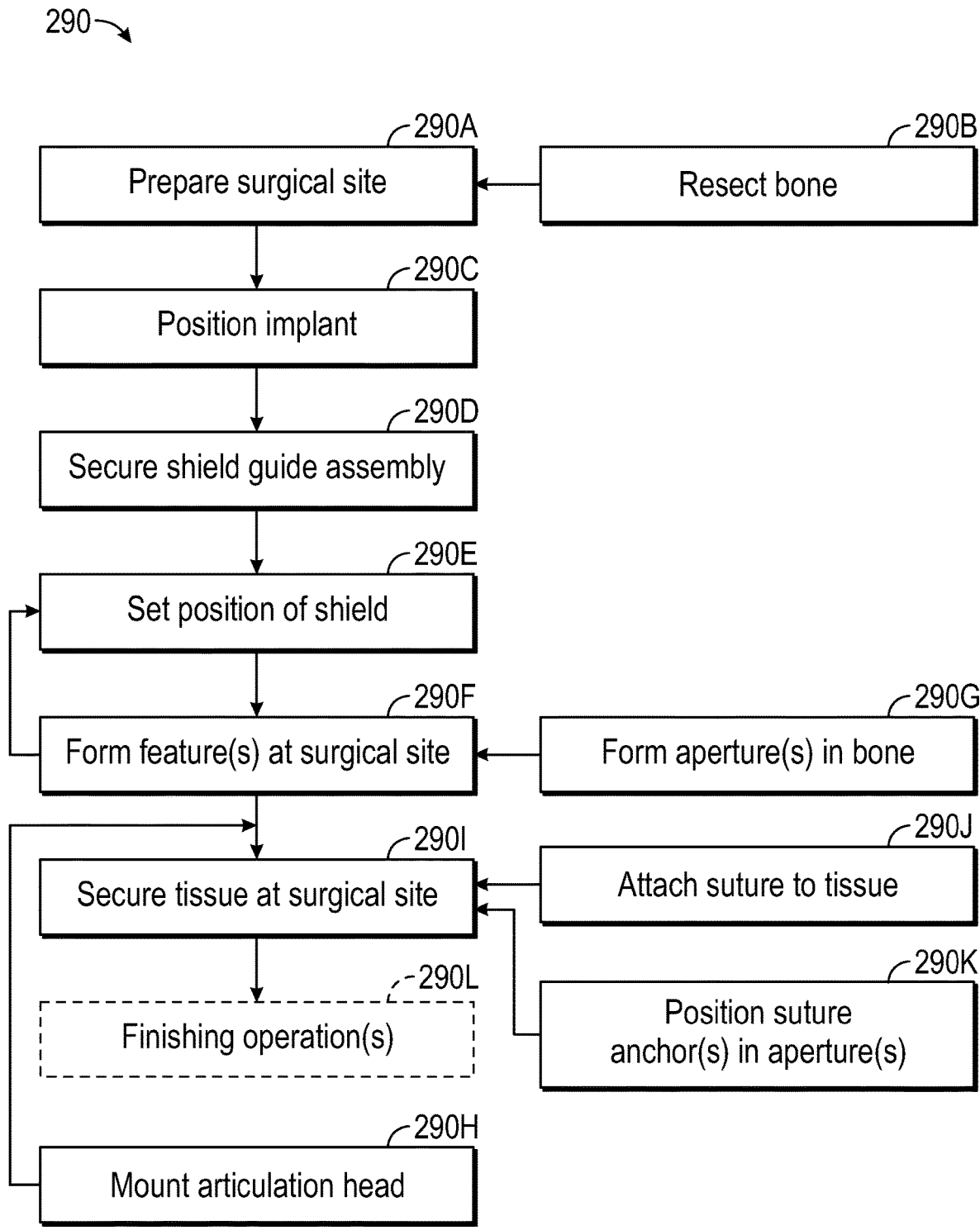
FIG. 10 illustrates an exemplary method of installing an orthopaedic implant system at a surgical site.

FIG. 10 illustrates an exemplary method of installing an orthopedic implant in a flow chart 290. The method 290 may be utilized to perform an arthroplasty for restoring functionality to a joint such as a shoulder having advanced cartilage disease, for example. The method 290 may be utilized with the shield guide assembly 20 and any of the orthopedic implants disclosed herein. Method 290 may be utilized to attach any tissue disclosed herein, including soft tissue such as tendons, ligaments and joint capsules. The tissue may be one of the rotor cuff tendons of a patient including a supraspinatus, infraspinatus, teres minor and/or subscapularis tendon. Fewer or additional steps than are recited below could be performed within the scope of this disclosure, and the recited order of steps is not intended to limit this disclosure.

Figure 11:
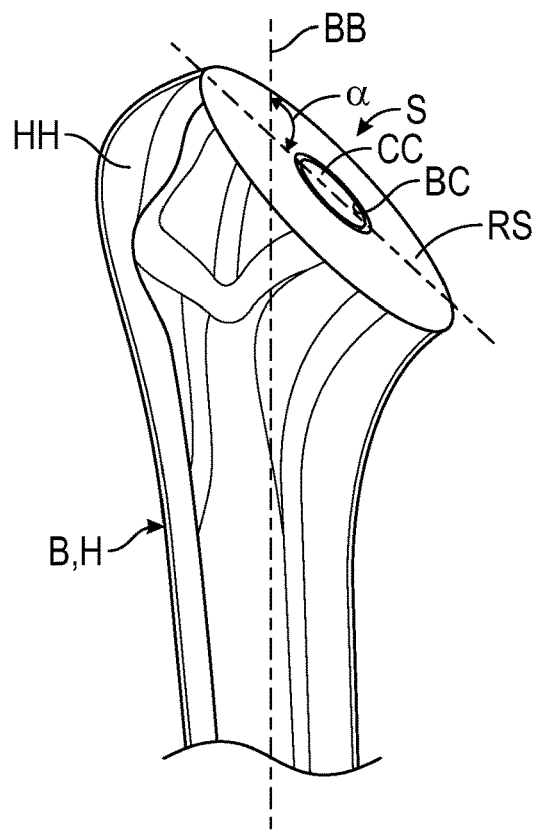
FIG. 11 illustrates a resected bone.

Referring to FIG. 11, with continuing reference to FIG. 10, a surgical site S may be prepared at step 290A. The surgical site S may be a joint, such as a shoulder joint including a glenoid G and humerus H (see, e.g., FIG. 15). The surgical site S may be established along bone B associated with an articular surface of the shoulder joint, such as a humeral head HH of the humerus. One or more operations can be performed to prepare the surgical site S, such as one or more reaming, milling and drilling operations to establish a desired geometry of the surgical site S.

Step 290A may include resecting a portion of the bone B at step 290B to establish a resected surface RS. Step 290B may include excising a portion of the humerus along the humeral head HH at a resection angle α relative to an axis BB of the bone B to establish the resected surface RS. The bone B may be resected utilizing one or more cutting instruments and guide blocks, for example.

Figure 12:
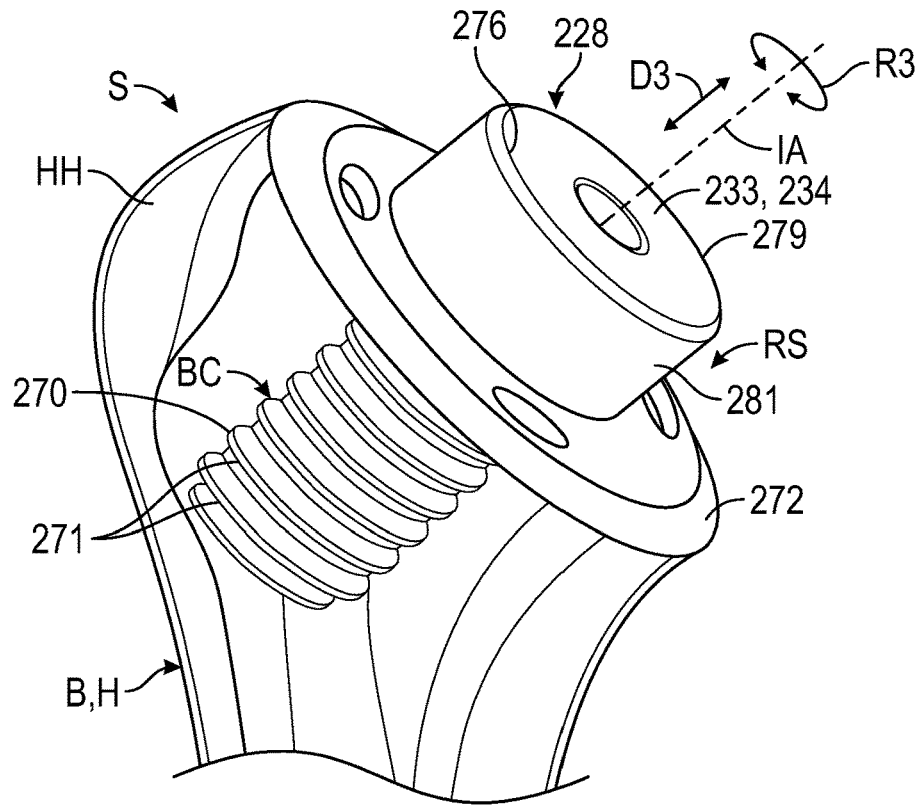
FIG. 12 illustrates an implant positioned along the resected bone of FIG. 11.

Step 290A may include forming a bone cavity BC along the resected surface RS and into the bone B. The bone cavity BC may be an annulus, as illustrated in FIG. 11. The bone cavity BC may be dimensioned to receive at least a portion of an implant body 233 of an implant 228, as illustrated in FIG. 12. In other implementations, a core CC may be removed such that the bone cavity BC is substantially hollow. Various techniques for forming the bone cavity BC may be utilized, such as impacting an annular coring template into the resected surface RS, or a reaming or drilling operation.

Referring to FIG. 12, with continuing reference to FIG. 10, the implant 228 may be positioned at least partially in the bone B at step 290C. The implant 228 may be a stemless implant. Other implants may be utilized with the method 290 and the shield guide assembly 20, including implants having an elongated stem received a humeral canal and any of the implants disclosed herein. Step 290C may include embedding at least a portion of the implant body 233 in the resected surface RS subsequent to resecting the bone B. A trunnion 272 may be moved into engagement or otherwise positioned along the resected surface RS.

The implant body 233 may be positioned at least partially in the bone cavity BC, which may occur subsequent to positioning the trunnion 272. The implant body 233 may be moved in the direction D3 along an implant axis IA and at least partially into a passage 276 of the trunnion 272 until a collar 279 of the implant body 233 abuts a main body 281 of the trunnion 272. Step 290C may include rotating the implant body 233 in a direction R3 about the implant axis IA to cause one or more threads 271 to fixedly attach or otherwise secure the implant body 233 in the bone B along the bone cavity BC.

Figure 13:
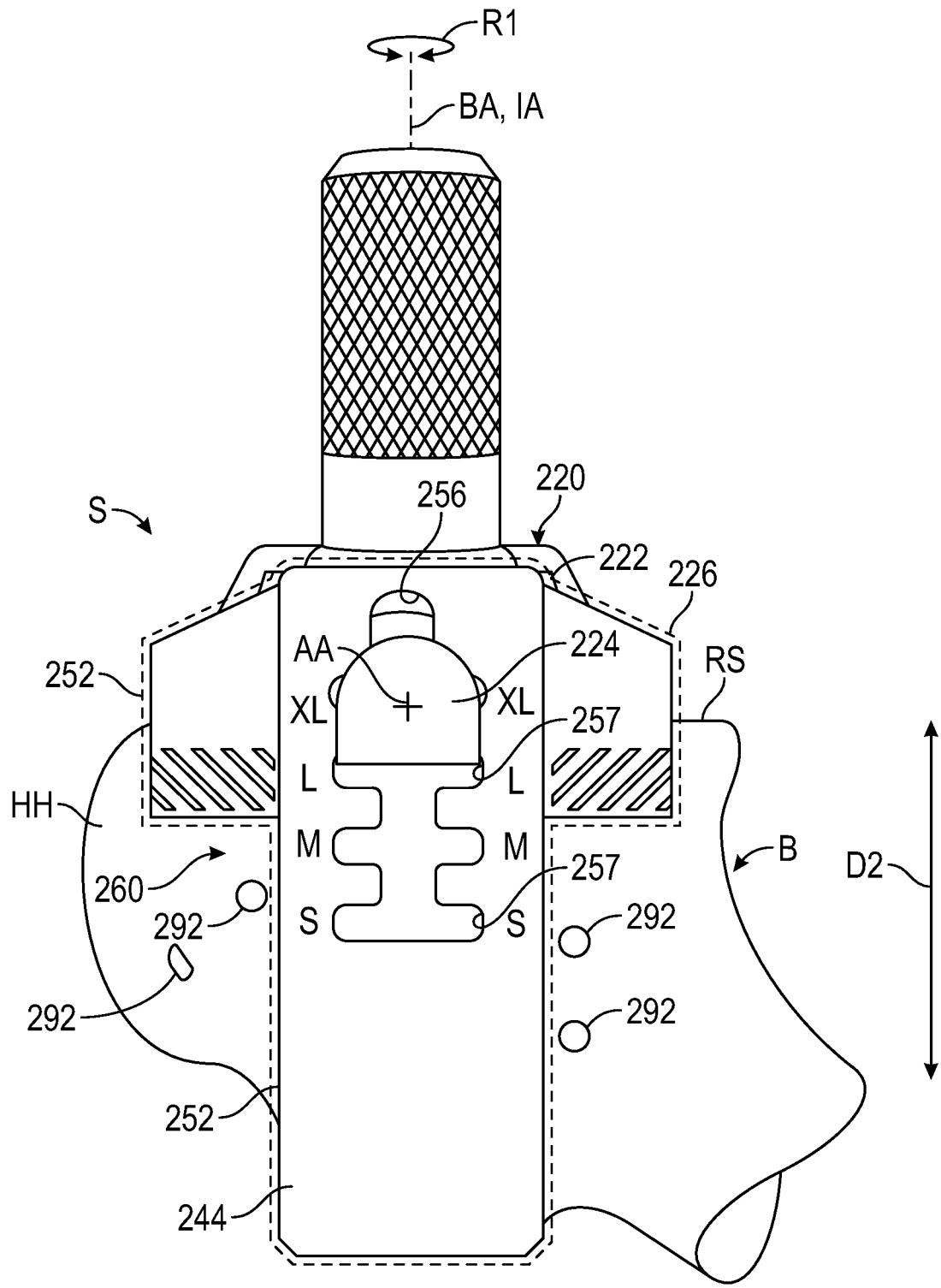
FIGS. 13-14 illustrate an exemplary shield guide assembly positioned relative a surgical site.
Figure 14:
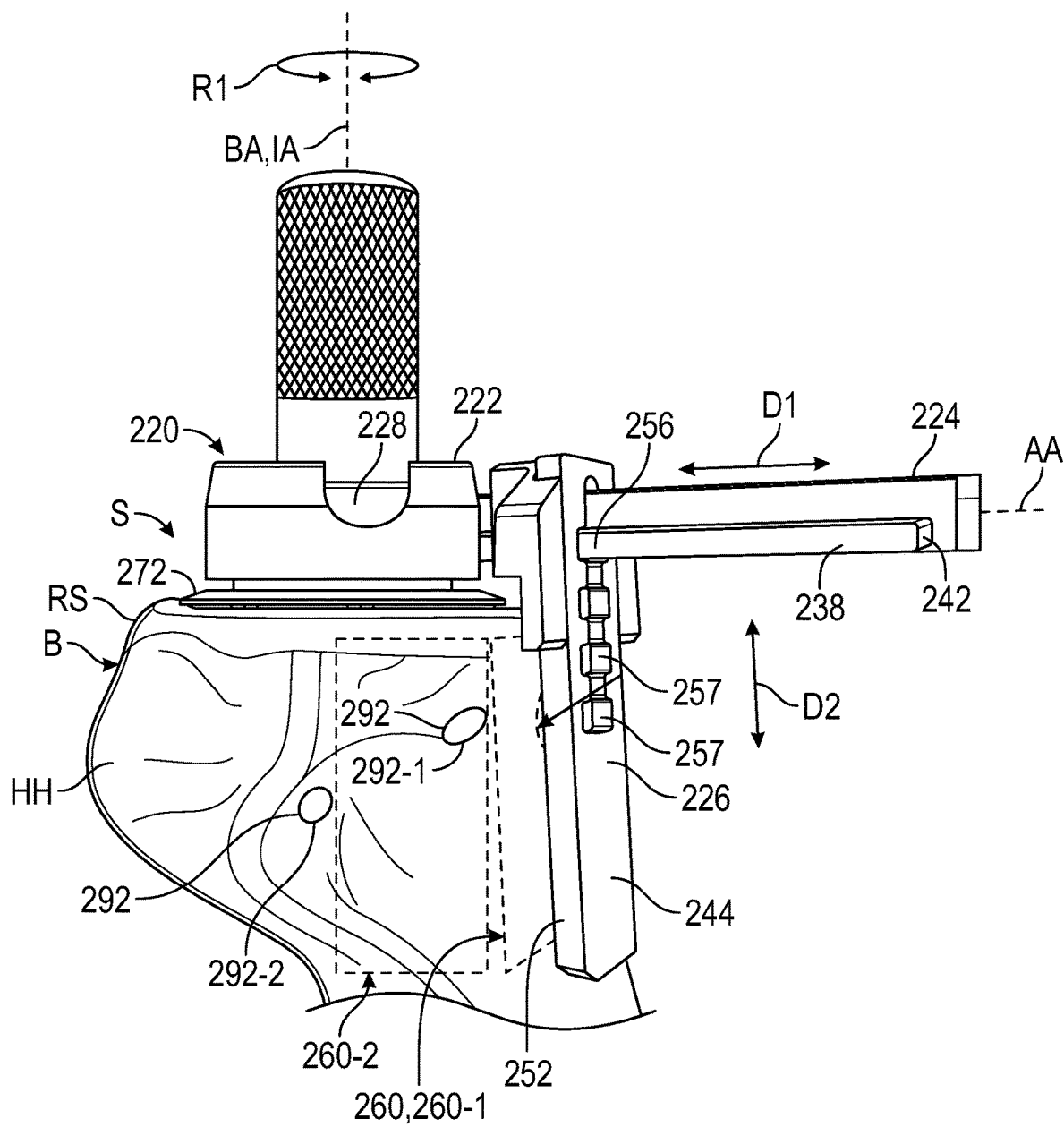

Referring to FIGS. 13-14, with continuing reference to FIG. 10, at step 290D a shield guide assembly 220 is releasably secured to the implant 228 to at least partially block access to a localized bone surface region 260 along the surgical site S (see FIG. 14). The shield guide assembly 220 may include a base 222, a guide arm 224 and a shield 226. Step 290D may include mounting the base 222 to the trunnion 272 or another portion of the implant 228, as illustrated in FIG. 14. In other implementations, the assembly 220 may be mounted directly to the implant body 233 (FIG. 12). The assembly 220 may be secured to the implant 228 such that the guide arm 224 is be cantilevered from a periphery of the base 222.

At step 290E, a position of the shield 226 may be set relative to the implant 228. Step 290E may include aligning a shield body 244 of the shield 226 with a selected T-shaped slot 257 in the guide arm 224, and then moving the shield 226 in a direction D2 to set the radial position of the shield 226 relative to the arm axis AA of the guide arm 224. Step 290E may include inserting one or more rails 238 of the guide arm 224 into a selected one of the T-shaped slots 257 to set the respective radial position of the shield 226. The rails 238 and slots 257 may be dimensioned to limit relative radial movement of the shield 226 relative to the arm axis AA such that the shield 226 sits on the guide arm 224 at a substantially constant height along a length of the rails 238.

Step 290E may include rotating the shield 226 in a direction R1 about the implant axis IA to set a circumferential position of the shield 226 relative to the implant 228 (FIG. 12). The assembly 220 may be dimensioned such that the shield 226 is rotatable approximately 360 degrees about the base axis BA to block access bone B surrounding the implant 228. In some implementations, the assembly 220 may be dimensioned such that the shield 226 is rotatable less than 360 degrees about the base axis BA, such as equal to or less than about 180 degrees.

Step 290E may include moving the shield 226 in a direction D1 along a length of the guide arm 224 to set a position of the shield 226 relative to the implant 228. Moving the shield 226 in the direction D1 along the guide arm 224 may occur such that the shield 226 abuts the bone B along the bone surface region 260 in the set position, as illustrated in FIG. 14 (see also FIG. 2). The bone surface region 260 may be associated with a projection of the shield perimeter 252 (252, 260 respectively shown in dashed lines in FIGS. 13-14 for illustrative purposes, see also FIG. 6). The shield body 244 may be dimensioned to block access through the shield body 244 onto the bone surface region 260 in the set position.

Figure 15:
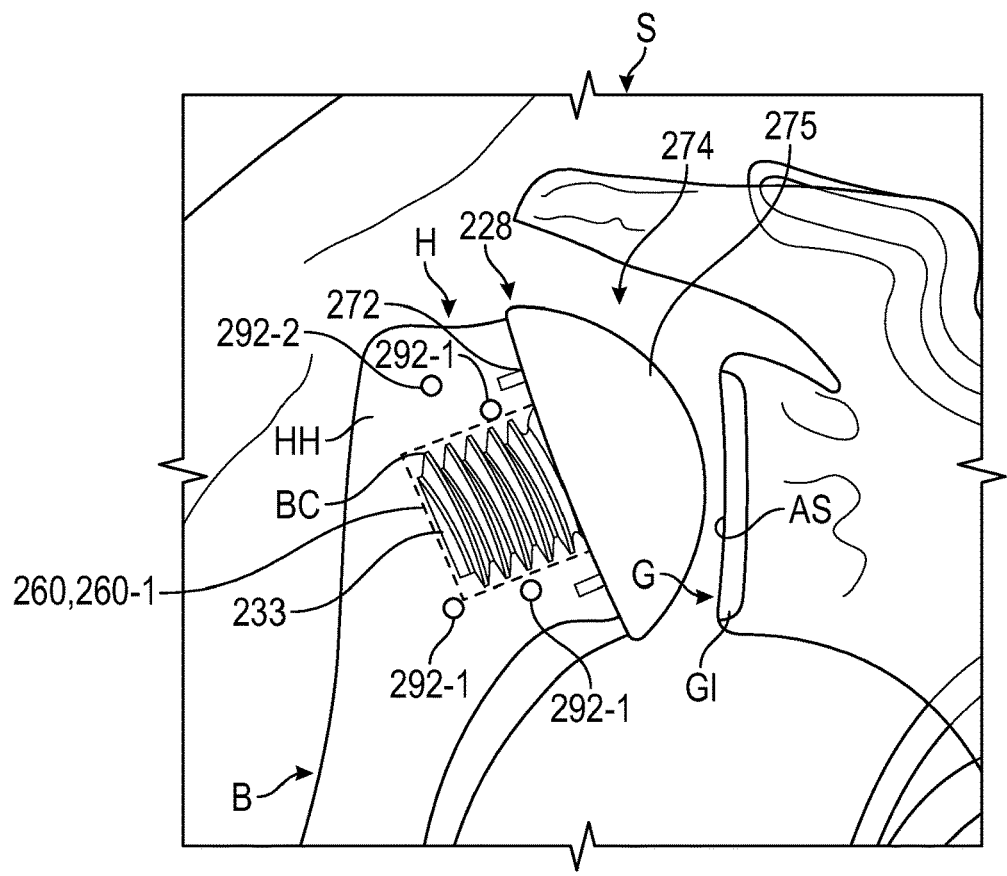
FIG. 15 illustrates the implant of FIG. 12 positioned at the surgical site.

At step 290F, one or more features may be formed at the surgical site S adjacent to the implant 228 while the assembly 220 is secured to the implant 220. Step 290F may occur subsequent to setting a position of the shield 226 at step 290E. The features may include recesses or apertures 292 configured to receive a respective fastener such as a suture anchor. The apertures 292 and other features may be formed utilizing various techniques, such as drilling, punching, inserting a needle, etc., into the bone B. Step 290G may include forming one or more apertures 292 in the bone B adjacent to the bone surface region 260 and shield 226, as illustrated in FIGS. 13-14. The apertures 292 may be formed in the humeral head HH outwardly of the shield perimeter 252 and bone surface region 260, as illustrated by FIGS. 14-15. Four apertures 292 formed in the humeral head HH are shown for illustrative purposes. However, a different number of apertures 292 such as only one or two apertures 292 may be formed in bone B along the surgical site S while the shield guide assembly 220 is secured to the implant 228. Step 290F may include forming one or more apertures 292-1 associated with a first bone surface region 260-1 corresponding to a first circumferential position of the shield 226 with respect to the base axis BA, rotating the shield 226 in the direction R1 to a second, different circumferential position at step 290E associated with a second, different bone surface region 260-2, and then forming one or more apertures 292-2 adjacent to the second bone surface region 260-2, as illustrated in FIG. 14 (see also FIG. 15). The assembly 220 may be removed from the surgical site S subsequent to forming the features 292.

Referring to FIG. 15, with continuing reference to FIG. 10, an articulation head 274 may be mounted to the implant body 233 to secure the articulation head 274 to the bone B at step 290H. Step 290H may occur such that an end portion of the implant body 233 is trapped between the trunnion 272 and articulation head 274 (see also FIG. 8). The articulation head 274 may include an articulating face 275 dimensioned to interface with an opposed articular surface AS. The articular surface AS may be associated with a glenoid G or a glenoid implant GI. The articulating face 275 may have a generally convex geometry as illustrated in FIG. 15, or may have a generally concave geometry.

Figure 16:
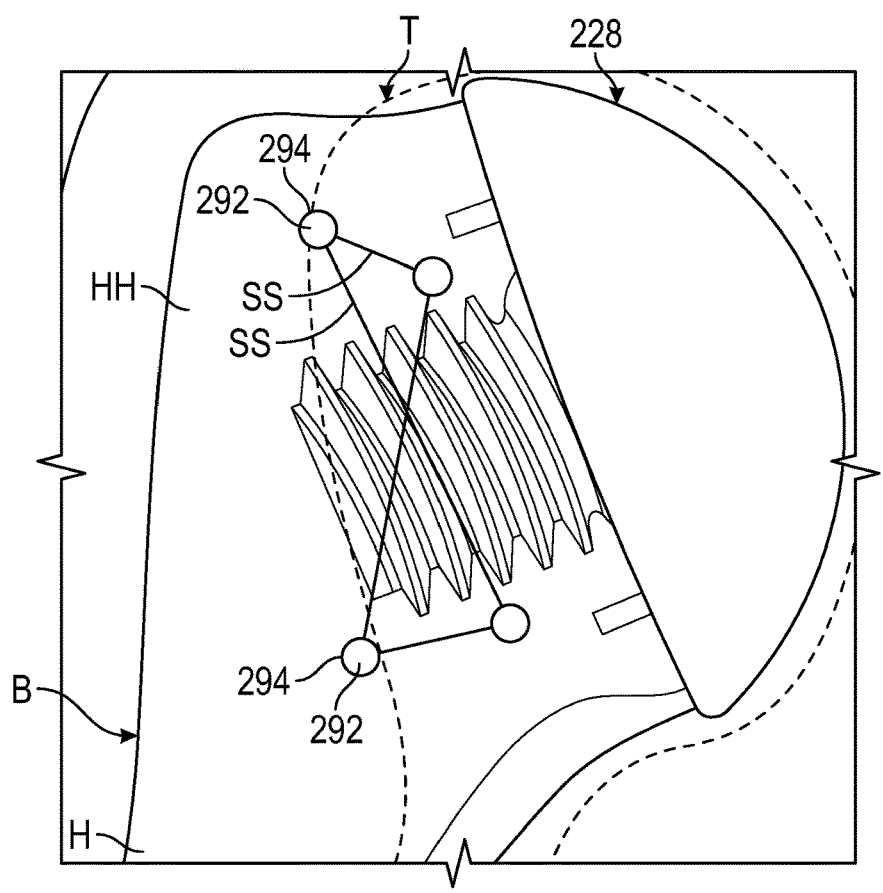
FIG. 16 illustrates tissue attached to the surgical site.

Referring to FIG. 16, with continuing reference to FIG. 10, at step 290I tissue T may be reattached or otherwise secured to the bone B along the surgical site S. The tissue T is shown in dashed lines in FIG. 16 for illustrative purposes. Step 290I may include attaching one or more lengths of the suture SS to an end portion of the tissue T at step 290J. The tissue T may include any tissue disclosed herein, including a tendon, ligament, or joint capsule. The tissue T may be one of the rotor cuff tendons including a supraspinatus, infraspinatus, teres minor and/or subscapularis tendon associated with a humerus H of the patient. Step 290I may occur subsequent to removing the assembly 220 from the surgical site S. Step 290A may include peeling or otherwise moving a portion of the tissue T away from the humeral head HH to provide access for positioning the implant 228. Step 290I may include moving the portion of tissue T over the articulating head 274 and to a position that substantially approximates an initial position of the tissue T prior to placement of the implant 228.

Step 290I may include securing the tissue T with one or more fasteners 294 affixed or otherwise secured in the bone B. Step 290I may include positioning one or more fasteners 294 in the respective apertures 292 to secure the tissue T to the bone B at step 290K. Step 290K may include positioning the fasteners 294 in the respective apertures 292 to secure the tissue T such as a subscapularis tendon to the humeral head HH of the humerus. Example fasteners can include anchors comprising various materials such as polyether ether ketone (PEEK), metallic and biocomposite materials, suture material, other natural and synthetic materials, and/or one or more sutures.

Figure 17:
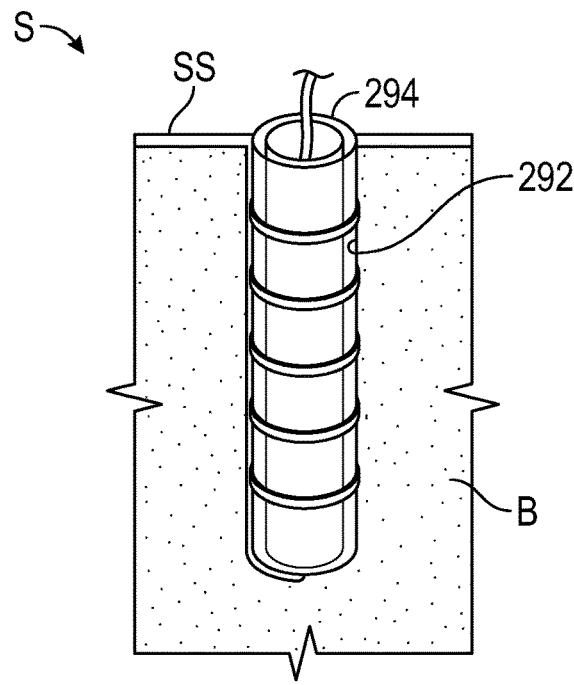
FIG. 17 illustrates a fastener positioned in an aperture.

The fasteners 294 may be suture anchors secured to the suture SS, for example. Step 290K may include at least partially inserting the fasteners 294 in respective apertures 292 to secure the suture SS at respective positions along the surgical site S. The fasteners 294 may have various geometries and configurations. For example, the fasteners 294 may have one or more threads or ribs to establish an interference fit with surfaces along the respective aperture 292, as illustrated by FIG. 17.

Figure 18:
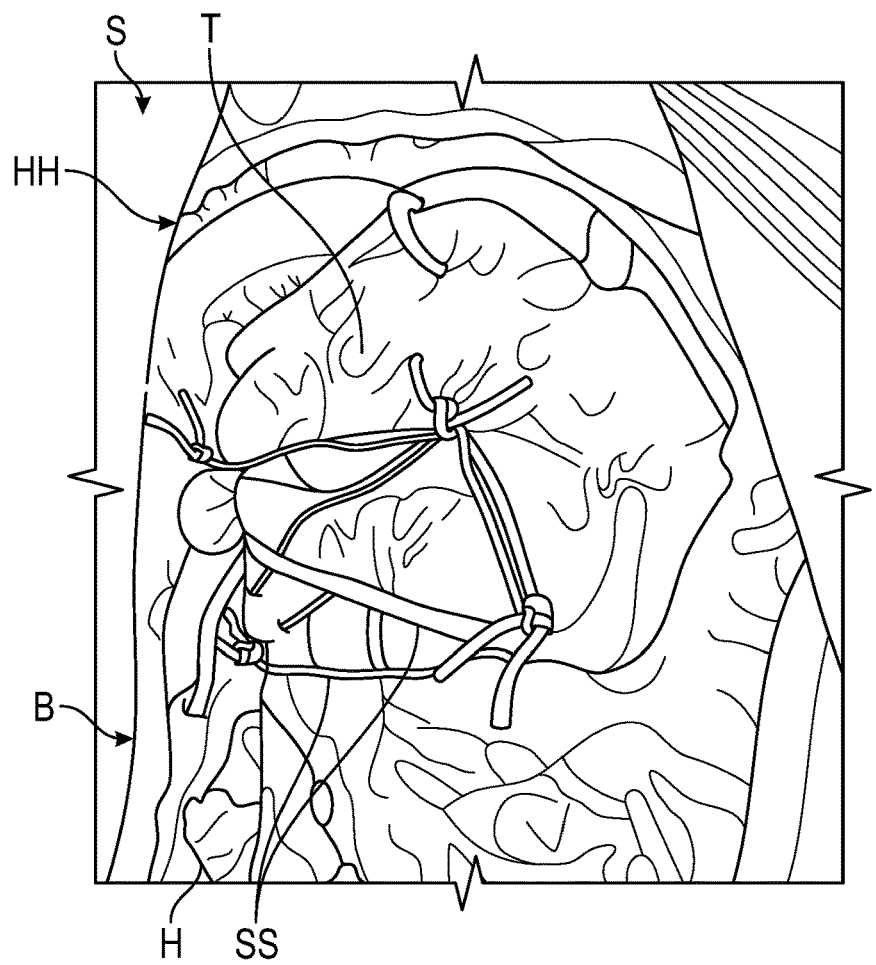
FIG. 18 illustrates a view of a completed repair of the tissue attached in FIG. 16.

Various techniques may be utilized for securing the tissue T at step 290I. In some implementations, the tissue T may be secured to the bone B utilizing a double row technique as illustrated in FIG. 16. Two rows of apertures 292 may be formed along the surgical site S outwardly of the respective bone surface region 260 associated with a projection of the shield perimeter 252 (see FIGS. 13-15). Fasteners 294 are situated in the respective apertures 292 to secure the suture SS and tissue T to bone B along the surgical site S. The suture SS may be arranged in a generally X-shaped pattern between the two rows of fasteners 294. In other implementations, step 290I may include performing a single row technique to secure the tissue to the bone B in which a pair of apertures 292 are formed to secure respective fasteners 294. FIG. 18 illustrates a completed repair including attachment of the tissue T as a result of step 290I, in which the tissue T is a subscapularis tendon reattached to the humeral head HH. One or more finishing operations may be performed at step 290L, including enclosing the surgical site S.

The novel shield guide assembly and methods of this disclosure may be utilized to block access to portions of a bone surrounding an embedded implant, which may reduce a likelihood of contacting or perforating the implant bone during formation of one or more features in close proximity to the implant. The shield guide assembly may be positioned circumferentially about the implant and/or at one or more heights to provide versality in selection of various implant geometries and to accommodate the respective bone profile of the patient. Apertures and other features may be formed in close proximity to the implant to provide improved bone purchase and fixation of a tendon or other tissue.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure.

What is claimed is:

1. A shield guide assembly for an orthopaedic procedure comprising:
   a base configured to be releasably secured to an implant;
   an elongated guide arm extending lengthwise along an arm axis from the base; and
   a shield carried by the guide arm, the shield translatable along a length of the arm axis to adjust a distance between the shield and the base, wherein the guide arm interconnects the shield and the base, the shield includes a shield body establishing a shield perimeter, and the shield body is dimensioned to block access through the shield body within the shield perimeter and onto an adjacent bone surface region associated with a projection of the shield perimeter.

2. The shield guide assembly as recited in claim 1, wherein the shield body includes at least one slot configured to slidably receive a portion of the guide arm along the arm axis.

3. The shield guide assembly as recited in claim 2, wherein a length of the guide arm has a T-shaped cross section.

4. The shield guide assembly as recited in claim 3, wherein the shield is translatable in an axial direction along the length of the arm axis to adjust the distance between the shield and the base, the at least one slot is a row of interconnected T-shaped slots corresponding to respective radial positions of the shield in a radial direction relative to the arm axis of the guide arm, and the length of the guide arm is insertable into each one of the T-shaped slots to set the respective radial position of the shield.

5. The shield guide assembly as recited in claim 4, wherein the shield body excludes any apertures between the row of slots and the shield perimeter.

6. The shield guide assembly as recited in claim 4, wherein:
the T-shaped slots are dimensioned such that the shield is adjustable at distinct intervals in the radial direction relative to the arm axis of the guide arm.

7. The shield guide assembly as recited in claim 6, wherein:
the shield body is dimensioned to block movement of the shield in the radial direction when the length of the guide arm is inserted into one of the T-shaped slots.

8. The shield guide assembly as recited in claim 1, wherein the base includes a recess configured to at least partially receive an end portion of the implant.

9. The shield guide assembly as recited in claim 8, wherein the base is rotatable about an implant axis of the implant to vary a circumferential position of the shield relative to the implant axis.

10. The shield guide assembly as recited in claim 1, wherein the shield is dimensioned to abut the adjacent bone surface region in an installed position.

11. The shield guide assembly as recited in claim 1, wherein the adjacent bone surface region is associated with a humerus.

12. The shield guide assembly as recited in claim 1, wherein:
a position of the guide arm is fixed relative to the base.

13. A shield guide assembly for an orthopaedic procedure comprising:
a base configured to be releasably secured to an implant;
a guide arm extending from the base; and
a shield carried by the guide arm, the shield moveable along a length of the guide arm to adjust a distance between the shield and the base, wherein the guide arm interconnects the shield and the base, and the shield includes a shield body is dimensioned to block access through the shield such that a projection of a perimeter of the shield body silhouettes a perimeter of the implant.

14. The shield guide assembly as recited in claim 13, wherein the base is rotatable about an implant axis of the implant to vary a circumferential position of the shield relative to the implant axis of the implant.

15. The shield guide assembly as recited in claim 14, wherein the perimeter of the shield is offset outwardly by a maximum distance of no more than 1 millimeter from the perimeter of the implant for substantially all positions along the perimeter of the implant below a bottom of the base relative to the implant axis.

16. The shield guide assembly as recited in claim 14, wherein the shield is moveable relative to the guide arm to vary a radial position of the shield relative to the implant axis.

17. The shield guide assembly as recited in claim 13, wherein the shield body is dimensioned to block access through the shield onto an adjacent bone surface region associated with a humerus.

18. A kit for an orthopaedic procedure comprising:
an implant including an implant body configured to be at least partially received in bone; and
a shield guide assembly comprising:
a base configured to be releasably secured to the implant;
a guide arm extending from the base; and
a shield carried by the guide arm, the shield translatable along a length of the guide arm to adjust a distance between the shield and the implant, wherein the guide arm interconnects the shield and the base, the shield includes a shield body establishing a shield perimeter, and the shield body is dimensioned to block access through the shield body within the shield perimeter and onto an adjacent bone surface region of the bone associated with a projection of the shield perimeter.

19. The kit as recited in claim 18, wherein the shield perimeter defines a shield width that is greater than an implant width of the portions of the implant configured to be received in bone.

20. The kit as recited in claim 18, wherein the implant body extends along an implant axis between first and second end portions, the base is configured to be secured to the first end portion, and the shield is rotatable about the implant axis to vary a circumferential position of the shield relative to the implant body in an installed position.

21. The kit as recited in claim 18, wherein:
the implant includes a trunnion configured to be secured to the implant body and an articulation head configured to be secured to the implant body;
the trunnion is configured to engage a resected surface along a humerus; and
the articulation head includes an articulating face dimensioned to interface with an opposed articular surface associated with a glenoid or a glenoid implant.

22. The kit as recited in claim 21, wherein a plurality of threads extend about a circumference of the implant body, and the plurality of threads are dimensioned to secure the implant body in bone.

23. A method of installing an orthopaedic implant, comprising:
positioning an implant in bone;
securing a shield guide assembly to the implant, wherein the shield guide assembly includes a base, a guide arm extending from the base, and a shield secured to the guide arm, the guide arm interconnecting the shield and the base, and including mounting the base to the implant;
moving the shield along a length of the guide arm to adjust a distance between the shield and the implant, wherein the shield includes a shield body that establishes a shield perimeter, the shield body is dimensioned to block access through the shield within a perimeter of the shield body and onto a bone surface region of the bone associated with a projection of the shield perimeter from the set position; and forming at least one aperture in the bone adjacent to the bone surface region and the shield.

24. The method as recited in claim 23, further comprising:
positioning a fastener in the at least one aperture to secure soft tissue to the bone.

25. The method as recited in claim 24, wherein the bone is a humerus, the fastener is a suture anchor, and the soft tissue includes a subscapularis tendon.

26. The method as recited in claim 24, wherein the bone is a humerus, and further comprising:
resecting the humerus along a humeral head to establish a resected surface, and then embedding at least a portion of the implant in the resected surface.

27. The method as recited in claim 23, further comprising:
rotating the shield about an implant axis of the implant to set a circumferential position of the shield relative to the implant;
wherein the moving step occurs such that the shield abuts the bone along the bone surface region in the set position; and
wherein the forming step occurs subsequent to the rotating step and the moving step.

28. The method as recited in claim 23, wherein the bone is a humerus, and further comprising:
resecting the humerus along a humeral head to establish a resected surface, and then embedding at least a portion of the implant in the resected surface.

29. The method as recited in claim 28, wherein:
the implant includes an implant body, a trunnion configured to be secured to the implant body, and an articulation head, wherein the articulation head includes an articulating face dimensioned to interface with an opposed articular surface associated with a glenoid or a glenoid implant; and
the step of positioning the implant includes moving the trunnion into engagement along the resected surface.

30. The method as recited in claim 29, wherein a plurality of threads extend about a circumference of the implant body, and the step of positioning the implant includes rotating the implant body about an implant axis to fixedly attach the implant body in the bone, and further comprising:
securing the articulation head to the trunnion to trap an end portion of the implant body between the trunnion and the articulation head.

* * * * *